United States Patent
Li et al.

(10) Patent No.: US 8,158,630 B2
(45) Date of Patent: Apr. 17, 2012

(54) APPLICATION OF 2,5 - DIHYDROXYMETHYL-3,6-DIMETHYL PYRAZINE AND ITS DERIVATES IN PHARMACY

(75) Inventors: Wei Li, Nanjing (CN); Long Chen, Nanjing (CN); Huimin Bian, Nanjing (CN); Hongmei Wen, Nanjing (CN); Zheng Liu, Nanjing (CN)

(73) Assignee: Nanjing University of Chinese Medicine, Nanjing, Jiangsu (CN)

( * ) Notice: Subject to any disclaimer, the term of this patent is extended or adjusted under 35 U.S.C. 154(b) by 290 days.

(21) Appl. No.: 12/703,131

(22) Filed: Feb. 9, 2010

(65) Prior Publication Data
US 2011/0195972 A1 Aug. 11, 2011

(51) Int. Cl.
*A61K 31/4965* (2006.01)
(52) U.S. Cl. .................................. 514/252.1
(58) Field of Classification Search ............. 514/252.1
See application file for complete search history.

(56) References Cited

FOREIGN PATENT DOCUMENTS
CN 200710092853.2 5/2007
CN 101134764 A 3/2008

OTHER PUBLICATIONS

Bundgaard, H., "Design of Prodrugs", Elsevier, 1985, 5 pages.
Widder, et al., "Drug and Enzyme Targeting", Methods in Enzymology, Academic Press 1985, vol. 112, pp. 309-396.
Krogsgaard-Larsen, et al., "A Textbook of Drug Design and Development", Second Edition, Harwood Academic Publishers, Chapters 13, "Design and application of Prodrugs" by G. Friis and H. Bundgaard, pp. 351-385.
Bundgaard, H., "Means to Enhance Penetration—Prodrugs to improve the deliverr of peptide drugs", Advanced Drug Delivery Review, 8 (1992) pp. 1-38.

*Primary Examiner* — Raymond Henley, III
(74) *Attorney, Agent, or Firm* — Christie, Parker & Hale, LLP

(57) ABSTRACT

An application of 2,5-dihydroxymethyl-3,6-dimethyl pyrazine and its derivatives in the preparation of drugs for the treatment of, prevention of, and/or protection from heart failure wherein the structural formula of the compound is as follows:

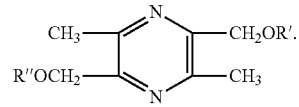

Formula I

8 Claims, 1 Drawing Sheet

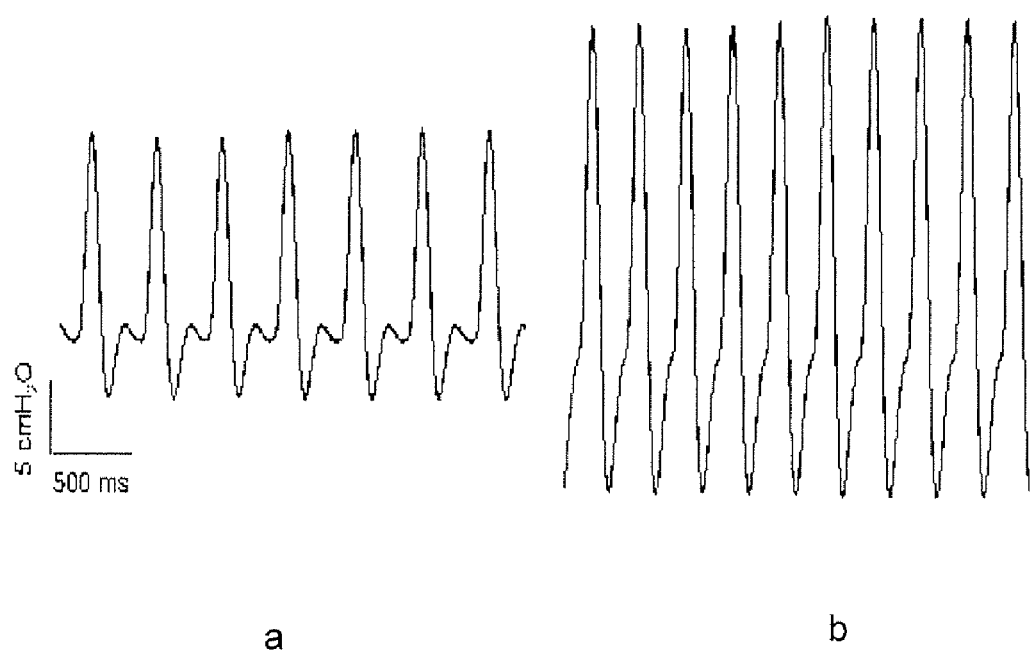
a        b

APPLICATION OF 2,5-DIHYDROXYMETHYL-3,6-DIMETHYL PYRAZINE AND ITS DERIVATES IN PHARMACY

FIELD

This invention refers to the compound 2,5-dihydroxymethyl-3,6-dimethyl pyrazine (Liguzinediol) and its derivatives, and in particular the usage of this compound Liguzinediol and its derivatives in the medical field.

BACKGROUND

Positive inotropic drugs have been widely used in the treatment of congestive heart failure, and in particular it is an important method for improving myocardial systolic functions by using positive inotropic drugs during the aggravation stage of diseases.

Currently, the conventional positive inotropic drugs mainly include:

(I) cAMP-Dependent Positive Inotropic Drugs Include:

1. β-receptor agonist: such drugs include dopamine, dobutamine and noradrenaline, which are used to improve the hemodynamic parameters of heart failure patients that suffer from myocardial function impairment in acute aggravation stage. Due to the signal dysfunction in early or late congestive heart failure (down-regulation of β-receptor and signal uncoupling), the application of β receptor agonists in the treatment of this kind of congestive heart failure only show relatively poor therapeutic effects. In addition, denopamine is also a kind of newly developed $β_1$ receptor partial agonist for oral administration.

2. Phosphodiesterase (PDE) III inhibitor: cAMP can directly regulate the contractility and diastole of normal myocardium and produce positive inotropic effect and positive lusitropic effect. These kind of drugs can increase cAMP by inhibiting PDE III and reducing cAMP degradation, and include: amrinone, milrinone, olprinone, vesnarinone and others.

3. Adenylate cyclase agonist: such drugs include forskolin, colforsin daropate hydrochloride (i.e. Adehl or NKH-477) and others.

(II) cAMP-Independent Positive Inotropic Drugs Mainly Include:

1. $Na^+/K^+$ATPase inhibitors: they can increase the influx of $Ca^{2+}$ by inhibiting $Na^+/K^+$-ATPase, such as digitalis cardiac glycoside including digoxin, digitoxin and lanatoside C.

2. Calcium sensitizer: such as pimobendam, sulmazole, thiadizinone and others, take effect on the coupled excitation-contraction process of myocardium and induce a transient $Ca^{2+}$ increase, and thus increase the sensitivity of muscular fibers or the responsibility to $Ca^{2+}$.

Great advancements have been achieved in the investigations on positive inotropic drugs during the past several decades, but currently available drugs have shown adverse effects in different degrees, particularly in cardiac arrhythmias and others, and the therapeutic effect is not satisfactory and thus it still needs further improvement.

Tetramethylpyrazine is one of the active ingredients of ligusticum chuanxiong hort, which has significant therapeutic effects on cardiovascular and cerebrovascular diseases with little side effects. Liguzinediol is the derivate (or derivative) of tetramethylpyrazine. The Chinese patent application 200710092853.2 disclosed that 2,5-di-(choline phosphate) methyl-3,6-dimethyl pyrazine, which is obtained by using liguzinediol as a precursor, can inhibit the activity of C-reactive protein (CRP). However, the positive inotropic activity of tetramethylpyrazine derivate has not been reported until now.

SUMMARY

An aspect of an embodiment of the present invention is directed toward an application of the compound 2,5-dihydroxymethyl-3,6-dimethyl pyrazine (Liguzinediol) and its derivatives for the treatment of, and/or prevention of (or protection from) heart failure.

An aspect of an embodiment of the present invention is directed toward the application or administration of 2,5-dihydroxymethyl-3,6-dimethyl pyrazine (Liguzinediol) and its derivatives for the treatment of, and/or prevention of (or protection from) heart failure, and the structural formula (Formula I) of said Liguzinediol or its derivative compound is as follows:

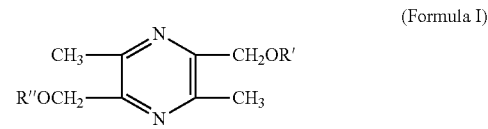

(Formula I)

In Formula I, R' and R" are selected from the following substituent groups:
Hydrogen;
Acyl and substituted acyl with 1-26 carbon atoms;
Alkyl and substituted alkyl with 1-26 carbon atoms;
Dioic acid monoacyl with 2-10 carbon atoms;
Phosphate monoacyl and its ester;
Sulphuric monoacyl and its ester;
Nitryl; and
Cross combinations of the above-mentioned groups.

In an embodiment of the invention, a method is provided for treating heart failure, the method comprising: administering a compound of 2,5-dihydroxymethyl-3,6-dimethyl pyrazine and/or derivatives thereof represented by Formula I:

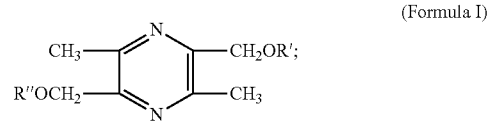

(Formula I)

wherein, R' and R" are selected from the group consisting of: hydrogen, acyl with 1-26 carbon atoms, substituted acyl with 1-26 carbon atoms; alkyl with 1-26 carbon atoms, substituted alkyl with 1-26 carbon atoms, dioic acid monoacyl with 2-10 carbon atoms, phosphate monoacyl, phosphate monoacyl ester, sulphuric monoacyl, sulphuric monoacyl ester, nitryl, and combinations thereof.

In another embodiment of the present invention, a method is provided for treating heart failure, wherein a compound having Formula I is administered, wherein R' and R" are each selected from the group consisting of hydrogen, acyl with 1-6 carbon atoms, alkyl with 1-6 carbon atoms, and dioic acid monoacyl with 2-6 carbon atoms.

In another embodiment of the present invention, a method is provided for treating heart failure, wherein a compound having Formula I is administered, and wherein at least one of R' and R" is an ester.

In another embodiment of the present invention, a method is provided for treating heart failure, wherein a compound having Formula I is administered, and wherein the compound is a pharmaceutically acceptable salt thereof.

In another embodiment of the present invention, a method is provided for treating heart failure, wherein a compound having Formula I is administered, wherein the compound is a pharmaceutically acceptable salt thereof, and wherein the pharmaceutically acceptable salt is a salt of an inorganic acid.

In another embodiment of the present invention, a method is provided for treating heart failure, wherein a compound having Formula I is administered, and wherein R' is hydrogen, R" is hydrogen and the administered compound is represented by Formula IA:

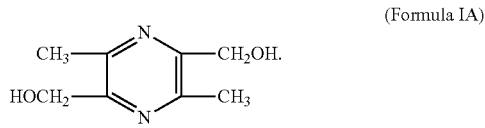

(Formula IA)

In another embodiment of the present invention, a method is provided for treating heart failure, wherein a compound having Formula I is administered, wherein R' is acyl, R" is acyl, and the administered compound is represented by Formula IB:

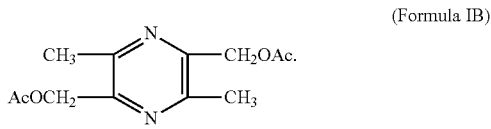

(Formula IB)

In another embodiment of the present invention, a method is provided for treating heart failure, wherein a pharmaceutical composition is administered comprising 2,5-dihydroxymethyl-3,6-dimethyl pyrazine and/or derivatives thereof represented by Formula I, wherein, R' and R" are selected from the group consisting of: hydrogen, acyl with 1-26 carbon atoms, substituted acyl with 1-26 carbon atoms; alkyl with 1-26 carbon atoms, substituted alkyl with 1-26 carbon atoms, dioic acid monoacyl with 2-10 carbon atoms, phosphate monoacyl, phosphate monacyl ester, sulphuric monoacyl, sulphuric monoacyl ester, nitryl, and combinations thereof.

BRIEF DESCRIPTION OF THE DRAWING

The accompanying drawing, together with the specification, illustrate exemplary embodiments of the present invention, and, together with the description, serve to explain the principles of the present invention.

The drawing shows the effects of compound 2 (Liguzinediol) (Formula 1A) on the left ventricular pressure of rats. In the drawing, a indicates the left ventricular pressure of rats before administration; and b indicates the left ventricular pressure of rats after administration.

DETAILED DESCRIPTION

In the following detailed description, only certain exemplary embodiments of the present invention are shown and described, by way of illustration. As those skilled in the art would recognize, the invention may be embodied in many different forms and should not be construed as being limited to the embodiments set forth herein.

Hereinafter, certain exemplary embodiments according to the present invention will be described with reference to the accompanying drawing.

Technical problem: the present invention, according to an embodiment, provides an application of the compound 2,5-dihydroxymethyl-3,6-dimethyl pyrazine (Liguzinediol) and its derivatives for the treatment, and prevention of (or protection from) heart failure.

Technical solution: the technical solution of this invention, according to an embodiment, is the application or administration of 2,5-dihydroxymethyl-3,6-dimethyl pyrazine (Liguzinediol) compound and its derivative compounds for the treatment, and/or prevention of (or protection from) heart failure, and the structural formula (Formula I) of said Liguzinediol compound or derivative compounds is as follows:

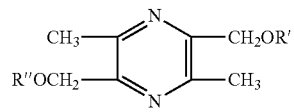

In Formula I, R' and R" are selected from the following substituent groups:
Hydrogen;
Acyl and substituted acyl with 1-26 carbon atoms;
Alkyl and substituted alkyl with 1-26 carbon atoms;
Dioic acid monoacyl with 2-10 carbon atoms;
Phosphate monoacyl and its ester;
Sulphuric monoacyl and its ester;
Nitryl; and
Cross combinations of the above-mentioned groups.

In one embodiment, R' and R" of the said liguzinediol or liguzinediol derivatives are selected from the group consisting of hydrogen, acyl with 1-6 carbon atom, alkyl with 1-6 carbon atom and dioic acid monoacyl with 2-6 carbon atoms.

In one embodiment, R' and R" of the said liguzinediol and liguzinediol derivatives are inorganic acid esters and their salts.

In one embodiment, the application of Liguzinediol and its derivatives in the preparation of drugs for the treatment and prevention of heart failure and the structural formula of said compound is shown in Formula 1A as follows:

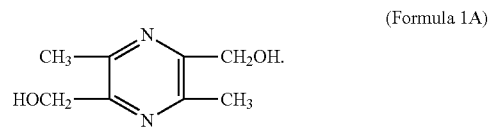

(Formula 1A)

In one embodiment, application/administration of 2,5-diacetoxymethyl-3,6-dimethyl pyrazine in the preparation of drugs for the treatment and prevention of heart failure and the structural formula of the said compound is shown in Formula 1B, as follows:

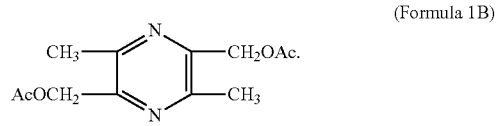

(Formula 1B)

The terminology "alkyl" refers to linear chain, branched chain or circular groups and their combinations, such as methyl, ethyl, propyl, isopropyl, butyl, s- and t-butyl, pentyl, hexyl, cyclohexyl, phenyl, benzyl and others.

The terminology "acyl" refers to acyl containing marked number of carbon atoms and linear chain, branched chain or circular structures, such as formyl, acetyl, propionyl, butyryl, isobutyryl, cyclohexyl-carbonyl, benzoyl and others.

The compounds mentioned in the present invention refer to effective ingredients with positive inotropic effects. The present invention includes positive inotropic pharmaceutical compositions and drugs for the treatment of heart failure. These diseases include congestive heart failure, particularly acute heart failure and serious terminal stage chronic heart failure when the disease is in the aggravation stage. The compounds mentioned in the present invention may also be effective in the treatment of heart failures that are induced by other reasons.

The compound in this invention can be used solely or in combination with other drugs in the treatments on the above-mentioned diseases.

The pharmaceutical composition of the compound in this invention should comprise at least a derivative of the compound represented by Formula I or the pharmaceutically acceptable salt of Formula I. A pharmaceutical composition according to the present invention may also comprise a kind of excipient, medium or carrier for medical use. The terminology "pharmaceutically acceptable salt" refers to the salt that is produced with a pharmaceutically acceptable non-toxic acid or alkali. The mentioned compounds of the invention includes the salt unless otherwise mentioned; the terminology "salt" refers to the salt that is produced with inorganic and/or organic acid and alkali; furthermore, the salt may include zwitter ions (internal salts), for example, a compound in formula I that not only includes the basic part such as pyrazine but also includes the acidic part such as carboxylic acid. The pharmaceutically acceptable salt (non-toxic, physiologically acceptable) do not lead to significant toxicity and biological activities, such as metal salts and amine salts having cations. However, other salts may also be useful. Therefore, other salts are also involved in the research scope of this invention. The separation and purification procedures that may be employed during the preparation process can be used to prepare the salts for the compound of Formula I, for example, by using ion exchange chromatography or employing the free base group of the compound of Formula I to react with a stoichiometric amount or excessive amount of organic or inorganic acids in proper solvents. The pharmaceutically acceptable non-toxic salts include those which originate from inorganic acid such as hydrochloric acid, hydrobromic acid, sulfuric acid, phosphoric acid, nitric acid, boric acid, thiocyanic acid and others. The salts that are produced by using organic acids include acetates (such as acetic acid or trihaloacetic acids, e.g. trifluoroacetic acid), propionates, butyrates, pivalates, caproates, heptylates, undecylates, cyclopentane propionates, benzoates, 3-phenpropionates, oxalates, succinates, maleates, adipates, alginate, ascorbates, aspartates, lactates, tartrates, citrates, camphorates, glucarates, fumarates, gluceptates, pectate, salicylates, picrates, nicotinate, glycerophosphates, sulfonates (for example, methanesulfonates, esylates, 2-hydroxyl esylates, benzenesulphonates, tosylates, 2-napsylates, camphorsulfonates and others), laurilsulfates and others.

Similarly, the salts of acidic compounds are produced by their reactions with proper inorganic or organic alkali. The typical salt groups include ammonium salts and alkaline-metal salts such as sodium, lithium and potassium salts; alkaline earths such as calcium and magnesium, barium, zinc and aluminium salts; the salts that are formed with organic alkali (such as organic amines) include trialkylamine, such as triethylamine, procaine, dibensylamine, N-benzyl-β-phenethylamine, 1-ephedra amine, N,N'-dibenzylidene diamine, dehydroabietylamine, N-ethyl piperidine, benzylamine, dicyclohexylamine, or similar pharmaceutically acceptable amines and the salts that are formed with amino acids such as arginine, lysine and others. Alkali groups containing nitrogen may react with elementary halogenated hydrocarbons (such as methyl, ethyl, propyl and butyl chlorides, bromides and iodides), dialkyl sulphate (such as dimethyl, dihexyl, dibutyl and dipentyl sulphates), long chain halogenated hydrocarbons (such as decyl, lauryl, tetradecyl, octadecyl chlorides, bromides and iodides), halogenated aromatic hydrocarbons (such as benzyl and phenethyl bromides) and others to conduct quaternization. The suitable salts include hydrochlorides, bisulfates, methanesulfonates or nitrates.

The present invention also refers to the precursor and solvents of the compounds. The terminology "pharmaceutical precursor" refers to the compound that can be transformed into formula (I) and/or a salt and/or a solvent. The examples for these precursor derivatives are shown in the following:
(a) Design of Prodrugs, edited by H. Bundgaard, (Elsevier, 1985) and Methods in Enzymology, Vol. 42, p. 309-396, edited by K. Widder, et al. (Acamedic Press, 1985); the entire content of which is herein incorporated by reference;
(b) A Textbook of Drug Design and Development, edited by Krosgaard-Larsen and H. Bundgaard, Chapter 5, "Design and Application of Prodrugs," by H. Bundgaard, p. 113-191 (1991); the entire content of which is herein incorporated by reference;
(c) H. Bundgaard, Advanced Drug Delivery Reviews, 8, 1-38 (1992); the entire content of which is herein incorporated by reference.

Since a compound containing a hydroxyl and carboxyl can form a biodegradable ester, it can be hydrolyzed in vivo and produce the compound of Formula I as a pharmaceutical precursor. Many hydrolytic cases take place due to the effects from digestive enzyme, and thus this kind of pharmaceutical precursor can be administered orally. If the ester itself is bioactive or it can be hydrolyzed in blood, parenteral administration can be carried out. The biodegradable ester of the compound of Formula (I) includes: $C_{1-6}$ alkyl benzyl, 4-methoxybenzyl, 2,3-indanyl($C_9H_9$—), phthaloyl, methoxymethyl, $C_{1-6}$ alkylacyloxy-$C_{1-6}$ alkyl, such as acetoxymethyl, pivaloyl oxymethyl or propionyloxymethyl, $C_{1-6}$ alcoxylformyloxy-$C_{1-6}$ alkyl, such as methoxyformyloxymethyl, or ethoxyformyloxymethyl, glyacyloxymethyl, phenylglyacyloxymethyl, (5-methyl-2-oxo-1,3-dioxolane-4-)-methyl and other adopted physiologically hydrolyzed esters, such as penicillin and cephalosporin.

The compounds of the present invention may be in free form (for example, not bound by a water molecule) or hydrate form.

The compounds of the embodiments of the present invention can be made into prescriptions with drug media or blended with diluents for oral, local and parenteral administration, such as intramuscular, intravenous or hypodermal injection, or blended diluents for inhalant spraying. The pharmaceutical formulations can be blended with solid or liquid media, dilutions and proper additaments by using conventional methods. The compounds can be produced into tablets, capsules, granules, powder, lozenges, aqueous or oily suspensions and others for oral administration. The compositions of the oral prescriptions can be prepared according to currently available methods for drug prescriptions, and the prescription may include one or more ingredients that are selected from sweeteners, toners and preservatives. For example, the tablets should include at least a compound of Formula I that is defined as above or its pharmaceutically acceptable salt, which can be mixed with excipients, such as lactose, starch, magnesium stearate, cellulose derivatives. The tablets may be coated or not coated in order to postpone disintegration and absorption, and thus retain the pharmacodynamic action for long term.

The drug prescription for oral administration in the present invention can be produced into hard capsules, in which the active ingredients are mixed with neutral solid diluents such as calcium carbonate and calcium phosphate; or it can be produced into soft capsules, in which the active ingredients are mixed with water, miscible solvents such as propenyl glycol, polyethylene glycol and ethanol, or oily solvents such as peanut oil and liquid paraffin. The content of the compounds in the prescription ranges from 0.01% to 100%, depending on the preparation process, dosage, administration route, indications, different diseases and other factors.

The dosage of the compounds of present invention ranges from 0.1 mg to 500 mg by parenteral administration in the form of injectable preparation, and it can also be orally administered in the form of tablets or capsules with the dosage ranging from 1 mg to 1000 mg. Adults with an average body weight of 60-70 kilograms can be administered once or more times a day. The unit dose composition of this drug prescription includes the active ingredient ranges from 1 mg to 500 mg, and the typical dosages are 1 mg, 5 mg, 10 mg, 25 mg, 50 mg, 100 mg, 200 mg, 300 mg, 400 mg and 500 mg.

The prescriptions and dosages containing the compounds of present invention that are used in the treatments on specific patients depend on many factors, including body mass, age, gender, medical conditions, serious degree of disease, administration route and frequency.

Beneficial effects: the present invention provides the application of 2,5-dihydroxymethyl-3,6-dimethyl pyrazine (Liguzinediol) and its derivates in the preparation of drugs for the treatment and prevention of heart failure.

EXAMPLES

Further detailed descriptions of this invention are carried out by following embodiments, and the embodiments are shown here in examples to better illustrate this invention and cannot be interpreted as limiting to the scope of the invention.

Example 1

The Efficacy on Isolated Heart of Rats

Procedure 1: Preparation of 2,5-dihydroxymethyl-3,6-dimethyl pyrazine (Compound 1) (Formula 1B)

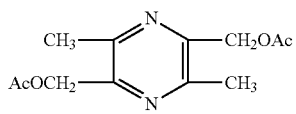

Anhydrous tetramethylpyrazine (6.80 g, 50 mmol), acetic acid (10 mL) and 30% hydrogen peroxide (mass concentration, 11 mL, 300 mmol) are mixed and heated at 98° C. for 12 h, and the mixture is cooled down to room temperature and then subjected to concentration in vacuo at 0.03 Mpa until it is 8 mL, subsequently 20% sodium hydroxide (mass concentration) is added to adjust the pH value to 9.0. The separated solid is then filtered and subjected to recrystallization with acetic ether, and white needle crystal of tetramethylpyrazine dinitrogenoxide is obtained (5.80 g, the yield is 68.7%). IR (KBr) cm$^{-1}$: 1523, 1504 (C=N), 1335 (C=C), 1306 (CH$_3$). EI-MS m/z (%): 168.1 (100), 152.1 (37.96), 151.1 (19.28), 135.1 (18.99), 134.1 (38.35), 93.1 (15.71), 53.0 (37.20).

Tetramethylpyrazine dinitrogenoxide (1.68 g, 10 mmol) is transferred to a round bottom flask and 12 mL acetic acid is then added. The mixture is heated at 100° C. for 4 h and excessive acetic anhydride is removed by evaporation in vacuo at 0.01 MPa. The residue is purified by silica gel column chromatography and 0.81 g light yellow liquid is thus obtained with a yield of 32.1%. IR (KBr) cm$^{-1}$: 1743 (C=O), 1458 (C=C), 1376 (C=N), 1236 (CH$_3$), 1059 (C—O). EI-MS m/z (%): 252.1 (0.94), 210.1 (21.32), 209.1 (17.15), 150.1 (95.39), 149.1 (100), 43.0 (20.14).

Procedure 2: Preparation of Liguzinediol (Compound 2) (Formula 1A)

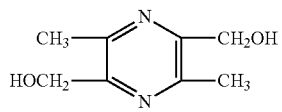

2,5-dihydroxymethyl-3,6-dimethyl pyrazine (compound 1) (2.52 g, 10 mmol) is fully mixed with a solution of 20% (mass concentration) sodium hydroxide (10 mL) and kept still for 1 h, then acetic acid is added to adjust the pH value to 7. The mixture is subjected to evaporation in vacuo at 0.03 MPa, and the residue is separated by silica gel column chromatography, thus white needle crystal is finally obtained (1.10 g, the yield is 65.5%). mp 116~117° C. UV (MeOH) $\lambda_{max}$ nm: 223, 278.5; IR (KBr) cm$^{-1}$: 3243 (—OH), 2858 (CH$_3$), 2922 (CH$_2$), 1425, 1365 (C=C), 1316, 1250 (C=N); $^1$H-NMR (DMSO-D6, 500 MHz) δ: 4.56 (4H, d), 5.15 (2H, t), 2.51 (6H, s); $^{13}$C-NMR (DMSO-D6, 500 MHz) δ: 151.15, 148.12, 62.85 (CH$_2$), 20.13 (CH$_3$); EI-MS m/z (%): 168.1 (76.38), 167.1 (28.90), 151.1 (11.95), 150.1 (18.66), 139.1 (100), 138.1 (26.9), 122.1 (13.41), 121.1 (61.54), 110.1 (15.87).

Procedure 3: Effects on the Cardiac Contractility of Isolated Hearts of Rats

Intraperitoneal injection of 1.2 g/kg urethane is carried out on rats and the hearts are collected. After the hearts are rinsed and cut in 100% oxygen saturated physiological saline at 0° C., they are connected to modified Langendorff heart perfusion equipments to conduct retrogressive perfusion via the aorta. The perfusate (in mmol/L) is NaCl 117, KCl 5.7, CaCl$_2$ 1.8, NaHCO$_3$ 4.4, NaH$_2$PO$_4$ 1.5, MgCl$_2$ 1.7, HEPES 20, Glucose 11, Creatine 10, Taurine 20, and NaOH is used to adjust the pH value to 7.3. The probe of the pressure receptor is inserted into the left ventricle via the left auricle, and BioAmp amplifier is used to record the left ventricular pressure, and the electrocardiogram is measured at the same time. The results are shown in Table 1. The results show that compound 1 and 2 (0.1 mmol/L) can significantly increase the cardiac contractility of isolated hearts of rats, and the differences of left ventricular systolic pressure (LVSP), left ventricular diastolic pressure (LVEDP), maximum value of left ventricular pressure increase (+dp/dtmax) and maximum value of left ventricular pressure decrease (−dp/dtmax) were statistically significant, and no statistically significant difference is found in the change in heart rate (see the drawing), and no heart dysrhythmia is found.

TABLE 1

The effects of compound 1 and 2 on the cardiac contractility of isolated hearts of rats

| Indexes | Compound 1 | | Compound 2 (Liguzinediol) | |
|---|---|---|---|---|
| | Before administration | After administration | Before administration | After administration |
| LVSP | 18.8 ± 9.8 | 26.1 ± 12.5* | 11.9 ± 2.6 | 26.9 ± 5.9** |
| LVEDP | −10.6 ± 5.8 | −14.4 ± 7.2* | −6.0 ± 1.2 | −13.0 ± 2.3** |
| +dp/dtmax | 669.6 ± 259.1 | 831.9 ± 268.2** | 415.3 ± 117.0 | 790.3 ± 251.6* |
| −dp/dtmax | −665.8 ± 273.0 | −884.9 ± 347.0* | −441.7 ± 128.5 | −763.5 ± 188.0** |
| Heart rate | 202.6 ± 44.1 | 191.6 ± 58.0$^\Delta$ | 145.0 ± 19.1 | 154.4 ± 28.8$^\Delta$ |

Comparison to those before administration,
*p < 0.05,
**p < 0.01,
$^\Delta$p > 0.5

The drawing shows the effects of compound 2 (Liguzinediol) (Formula 1A) on the left ventricular pressure of rats. In the drawing a shows the results before administration and b shows the results after administration.

Example 2

Effects on the Changes in Heart Functions and Hemodynamics of Rats

After the rats are paralysed with 20% ethyl urethane (urethane) (1 g/kg) and fixed on a thermostatical operation table on their backs, needle-electrodes for electrocardiogram are subcutaneously inserted from their extremities and the lead II echocardiogram (ECG) and the heart rate (HR) are measured by inputting into the multiplying channel device. The right common carotid artery is isolated from the inner side of sternocleidomastoid muscle after the echocardiogram and temperature (37° C.) become stable, and the right common carotid artery is ligated at its head end and left ventricular cannulation is carried out. It is connected with the polygraph via a pressure transducer to measure the heart function indexes of left ventricle, in the meantime, the right femoral vein is isolated and venous cannulation is carried out for the intravenous administration, and the non-inserted end is connected to a syringe that is filled with 40 IU/mL heparin physiological saline, the multi-channel physiological signal acquisition and processing system is used to record the data. After the measured indexes become stable, the data at one minute before the drug administration are recorded as the blank control, and Liguzinediol is dissolved in physiological saline and then use 5, 10 and 20 mg/kg respectively as the low, mediate and high dosage groups, and the results within one minute after the intravenous administration are shown in Table 2. The heart rate aberration that is induced by Liguzinediol is not found in the three dosage groups after administration.

The results show that 5, 10 and 20 mg·kg$^{-1}$ liguzinediol can significantly increase LVSP, +dp/dt$_{max}$, −dp/dt$_{max}$ and other heart function indexes and decrease LVEDP, indicating that liguzinediol can significantly increase the left ventricular contraction and improve the diastolic function of rat heart.

TABLE 2

Effects of Liguzinediol on the heart functions of normal rats $\bar{X} \pm s$, n = 10

| Indexes | 5 mg/kg | | 10 mg/kg | | 20 mg/kg | |
|---|---|---|---|---|---|---|
| | Before administration | After administration | Before administration | After administration | Before administration | After administration |
| LVSP | 122.8 ± 13.2 | 132.7 ± 9.1** | 122.5 ± 13.8 | 135.7 ± 10.9** | 121.2 ± 10.2 | 139.7 ± 4.6** |
| LVEDP | 9.1 ± 6.7 | 7.9 ± 6.3 | 10.1 ± 5.2 | 6.9 ± 6.1** | 12.1 ± 4.1 | 6.3 ± 4.8* |
| +dp/dtmax | 10272 ± 1496 | 12027 ± 1388** | 9831 ± 1409 | 11484 ± 1410** | 9716 ± 980 | 12347 ± 1030** |
| −dp/dtmax | −9156 ± 1284 | −10238 ± 1247** | −8138 ± 808 | −9667 ± 670** | −8138 ± 1161 | −9964 ± 1045** |

Comparison to those before administration,
*P < 0.05 and
**P < 0.01

Toxicity test. For the acute toxicity test with one single administration, Liguzinediol is produced into aqueous solution and intravenous injection administration is carried out via tail vein. The mice all survive when intravenous injection administration via tail vein is carried out in 1.5 g/kg, indicating that this compound has excellent safety.

While the present invention has been described in connection with certain exemplary embodiments, it is to be understood that the invention is not limited to the disclosed embodiments, but, on the contrary, is intended to cover various modifications and equivalent arrangements included within the spirit and scope of the appended claims, and equivalents thereof.

The invention claimed is:

1. A method of treating heart failure comprising:
administering a compound of 2,5-dihydroxymethyl-3,6-dimethyl pyrazine or derivatives thereof represented by Formula I:

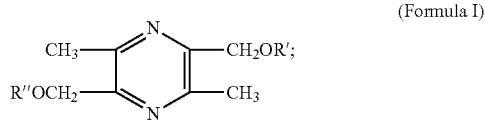

(Formula I)

wherein, R' and R" are selected from the group consisting of: hydrogen, acyl with 1-26 carbon atoms, substituted acyl with 1-26 carbon atoms; alkyl with 1-26 carbon atoms, substituted alkyl with 1-26 carbon atoms, dioic acid monoacyl with 2-10 carbon atoms, phosphate monoacyl, phosphate monacyl ester, sulphuric monoacyl, sulphuric monoacyl ester, nitryl, and combinations thereof.

2. The method of claim 1, wherein R' and R" are selected from the group consisting of hydrogen, acyl with 1-6 carbon atoms, alkyl with 1-6 carbon atoms, and dioic acid monoacyl with 2-6 carbon atoms.

3. The method of claim 1, wherein at least one of R' and R" is an ester.

4. The method of claim 1, wherein the administered compound is a pharmaceutically acceptable salt thereof.

5. The method of claim 4, wherein the pharmaceutically acceptable salt is a salt of an inorganic acid.

6. The method of claim 1, wherein R' is hydrogen, R" is hydrogen, and the administered compound is represented by Formula IA:

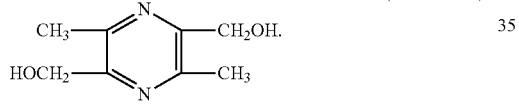

(Formula IA)

7. The method of claim 1, wherein R' is acyl, R" is acyl, and the administered compound is represented by Formula IB:

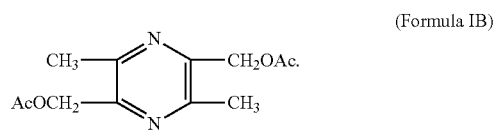

(Formula IB)

8. A method of treating heart failure comprising:
administering a pharmaceutical composition comprising: 2,5-dihydroxymethyl-3,6-dimethyl pyrazine and/or derivatives thereof represented by Formula I:

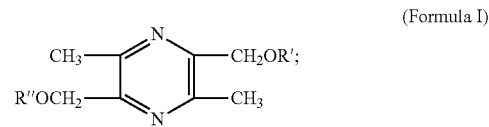

(Formula I)

wherein, R' and R" are selected from the group consisting of: hydrogen, acyl with 1-26 carbon atoms, substituted acyl with 1-26 carbon atoms; alkyl with 1-26 carbon atoms, substituted alkyl with 1-26 carbon atoms, dioic acid monoacyl with 2-10 carbon atoms, phosphate monoacyl, phosphate monacyl ester, sulphuric monoacyl, sulphuric monoacyl ester, nitryl, and combinations thereof.

* * * * *